US00PP08374P

United States Patent [19]

Cuthbertson

[11] Patent Number: Plant 8,374

[45] Date of Patent: Sep. 14, 1993

[54] SYNGONIUM PLANT NAMED INFRA-RED

[75] Inventor: Nicholas M. Cuthbertson, Kensington Park, Australia

[73] Assignee: Phytotech Australia Pty. Ltd., Edwardstown, Australia

[21] Appl. No.: 883,039

[22] Filed: May 13, 1992

[51] Int. Cl.[5] ..... A01H 5/00

[52] U.S. Cl. ..... Plt./88.1

[58] Field of Search ..... Plt./88.1

[56] References Cited

U.S. PATENT DOCUMENTS

P.P. 4,514 3/1980 Longoria ..... Plt. 88.1

*Primary Examiner*—James R. Feyrer

*Attorney, Agent, or Firm*—Foley & Lardner

[57] ABSTRACT

A new and distinct variety of *Syngonium podophyllum* named Infra-Red having the characteristics of full and compact habit, short internodes, lack of vining habit, upper leaf surface with a copper-orange color, retention of copper-orange leaf color as plants mature, ease of propagation, rapid growth, less inclination to damage at retail outlets due to lack of vines, and its tolerance to lower light levels which makes it adaptable to use in indoor plantings.

3 Drawing Sheets

The present invention is a new and distinct cultivar of *Syngonium podophyllum*, known by the cultivar name Infra-Red.

The new cultivar was discovered as a spontaneous mutation in a group of several hundred micropropagated plants grown in tissue culture in the greenhouses of Phytotech Australia, Edwardstown, South Australia, in 1986. Plants of *Syngonium podophyllum* were micropropagated in tissue culture using the well known methods taught by L. R. Miller and T. Murashige, "Tissue Culture of Tropical Foliage Plants", In Vitro, vol. 12, pp. 797–813 (1976), which is incorporated herein by reference.

The parent plant that actually produced Infra-Red was *Syngonium podophyllum* Maya Red, which had previously been used for pot plant production. The new mutation is the result of micropropagation of a parent Maya Red plant. Upon plant-out and subsequent growth the new cultivar was immediately recognized for its non-vining growth habit and better color retention.

The new cultivar was first successfully asexually reproduced by tissue at Phytotech Australia, Edwardstown, South Australia, by the inventor in 1986. The new cultivar has been maintained by means of continual propagation through tissue culture cycles of re-initiation, multiplication and plant-out under the name Infra-Red. Its shoots or clumps were subcultured every 4 weeks. No special treatment for rooting was required. Shoots or clumps were subcultured into liner trays containing commercial potting soil.

Horticultural examinations over subsequent generations of propagation clearly demonstrated that the combination of characteristics as herein disclosed for Infra-Red are firmly fixed and are retained through successive generations of asexual reproduction, with no changes in plant characteristics.

Infra-Red has not been observed under all possible environmental conditions. The phenotype may vary somewhat with variations in environment such as temperature, light intensity and day length, without, however, any variance in the genotype.

The following traits have been repeatedly observed and are the basic characteristics of Infra-Red. In combination, these traits distinguish it as a new and distinct cultivar:

(1) Infra-Red does not vine. Maya Red produces elongated shoots or shoot-runners.

(2) Infra-Red is a more densely bushed and compact variety, compared to the more singular and leggy Maya Red. Infra-Red produces an abundance of branches and leaves giving it a dense and full appearance.

(3) The upper surface of the mature Infra-Red leaf blades are copper-orange. The upper surfaces of the mature Maya Red Leaf blades are more copper to brick-red than Infra-Red.

(4) Unlike Maya Red, which loses its red leaf color as it matures and becomes ready for sale, Infra-Red retains its copper-orange leaf color.

(5) Infra-Red grows more vigorously than Maya Red.

(6) Infra-Red is less susceptible to damage at retail outlets because of its non-vining growth habit.

(7) Infra-Red tolerates lower light levels and therefore grows well indoors.

(8) All of the above characteristics together result in an outstanding new cultivar, and market research to date has indicated a probable wide acceptance of the new cultivar.

In the accompanying photographic sheets,

Sheet 1 is a color photograph illustrating in perspective view the new cultivar grown in a 7" pot for 39 weeks.

Sheets 2 and 3 are color photographs of the upper and lower leaf blade surfaces of the new cultivar, respectively. In each of these photographs on the left is an immature leaf and on the right is a mature leaf.

The following description is based on observations and measurements of 39 week-old Infra-Red grown in 7" pots in the greenhouses of Phytotech Australia Pty Ltd, Adelaide, Australia. Color references are made to The Royal Horticultural Society Colour Chart (RHS). Color values were taken in late August in Adelaide, South Australia, under natural light conditions.

DESCRIPTION OF THE PLANT

Botanical: *Syngonium podophyllum*, c.v. Infra-Red.

Origin: Spontaneous mutuation of *Syngonium podophyllum*, c.v. Maya Red.

Form: Compact, clumped habit, suitable for 4–6" pots, baskets (1 liner per pot) or interiorscape use; much more compact and somewhat shorter than Maya Red.

Shape: Compact form with rounded top growth; leaves hang loosely; leaves more abundant than Maya Red.

Growth: Vigorous, very hardy indoors; faster growing than Maya Red; branches from central shoot.

Stem: Stem size 0.5–1.0 cm. in diameter; stem somewhat oval in shape.

Root: Fibrous root system proportional in size to size of above-ground plant; root diameter 2–2.5 mm.

Internodes: Internodes from 0.5–1.0 cm. long.

Foliage:

*Quantity.*—Abundant; each branch has 4–5 leaves and the central plant has 6–8 leaves; quantity of foliage is much more abundant than that of Maya Red.

*Leaves.*—Shape: Mature leaf blades at the base are hastate or sagittate-peltate and at the blade apex are acuminate; as matures the blade goes from entire to palmate; margin cupped and wavy. Size: Mature leaf blades 12–16 cm. long and 4–6 cm. wide. Quantity: Profusely abundant. Texture: Herbaceous and smooth. Gloss: Sightly dull. Color: Upper surfaces of mature leaf blades copper-orange 182C-D with a thin green margin and a green midrib 146D; upper surfaces of immature leaf blades copper-red 182C-D with a green midrib 145C; Bottom surfaces of mature leaf blades are green 146B with a green midrib 145C; bottom surfaces of immature leaf blades are green 147C with as green midrib. Petioles: Averaging 13–19 cm. in length, color is green 146D; Veins: Fairly prominent, slightly recessed on upper surface and slightly protruding on under surface, 3 primary lateral veins.

Flowers: None.

Disease Resistance: Good as compared with the parent cultivar or other Syngonium cultivars grown under the same conditions.

Other Characteristics:

*Color retention.*—A distinctive characteristic of Infra-Red is its retention of the copper-orange leaf color as the plant matures. Maya Red loses its red leaf color just as it matures and is ready for sale while Infra-Red retains its copper-red leaf color.

*Compact and dense habit.*—A distinctive characteristic is the compact and dense habit with short internodes and increased branch number compared to Maya Red.

*Adaptability.*—Infra-Red does not cascade or vine. It is adaptable to 4–6" pots and baskets and is particularly durable indoors where it grows vigorously.

Chart A compares certain characteristics of Infra-Red with the same characteristics of the parent, and closest known cultivar, Maya Red. The compactness and unique upper leaf surface color of Infra-Red will be particularly apparent from the comparative measurements and observations.

CHART A

| | |
|---|---|
| **MAYA RED** | |
| PLANT: | |
| Form: | Vining habit; suitable for 4–6" pots or hanging baskets; less compact and less dense than Infra-Red; 3–6 branches when grown in a 6" pot. |
| Growth: | Less vigorous growth rate than Infra-Red. |
| Root: | Fibrous root system proportional in size to size of above-ground plant; root diameter 2–2.5 mm. |
| Stem: | 0.5–0.8 cm. in diameter. |
| Internodes: | 0.5–3.0 cm. long. |
| FOLIAGE: | |
| Size: | Mature leaf blades 12–16 cm. long and 5–7 cm. wide. |
| Quantity: | Openly abundant. |
| Shape: | Mature leaf blade at base is hastate or sagittate-peltate; blade apex is acuminate; as the leaf matures the leaf margin viewed from the top changes from entire to palmate; margin of blade cupped and wavy. |
| Texture: | Herbaceous, slightly dull, smooth. |
| Color: | Upper surface is more copper to brick-red than Infra-Red, thin green margin; lower surface green; loses red leaf color as plant matures. |
| Petioles: | Averaging 20–22 cm. long. |
| **Infra-Red** | |
| PLANT: | |
| Form: | Non-vining habit; compact; suitable for 4–6" pots or hanging baskets; more compact and dense than Maya Red; 6–12 branches when grown in a 6" pot. |
| Growth: | More vigorous growth rate than Maya Red. |
| Root: | Fibrous root system proportional in size to size of above-ground plant; root diameter 2–2.5 mm. |
| Stem: | 0.5–1.0 cm. in diameter |
| Internodes: | 0.5–1.0 cm long. |
| FOLIAGE: | |
| Size: | Mature leaf blades 12–16 cm. long and 4–6 cm. wide; margin cupped and wavy. |
| Quantity: | Profusely abundant. |
| Shape: | Mature leaf blade at base is hastate or sagittate-peltate; blade apex is acuminate; as the leaf matures the leaf margin viewed from the top changes from entire to palmate; margin of blade cupped and wavy. |
| Texture: | Herbaceous, slightly dull, smooth |
| Color: | Upper surfaces of mature leaf blades copper-orange 182C-D with a thin green margin and a green midrib 146D; upper surfaces of immature leaf blades copper-orange 182C-D with a green midrib 145C; Bottom surfaces of mature leaf blades are green 146B with a green midrib 145C; bottom surfaces of immature leaf blades are green 147C with a green midrib; retains copper-orange leaf color as plant matures. |
| Petioles: | Averaging 13–19 cm. in length, green color. |

I claim:

1. A new and distinct variety of *Syngonium podophyllum* named Infra-Red as illustrated and desribed, and particularly characterized by its full and compact habit, short internodes, lack of vining habit, upper leaf surface with a copper-orange color, retention of copper-orange leaf color as plants mature, ease of propagation, rapid growth, less inclination to damage at retail outlets due to lack of vines, and its tolerance to lower light levels which makes it adaptable to use in indoor plantings.

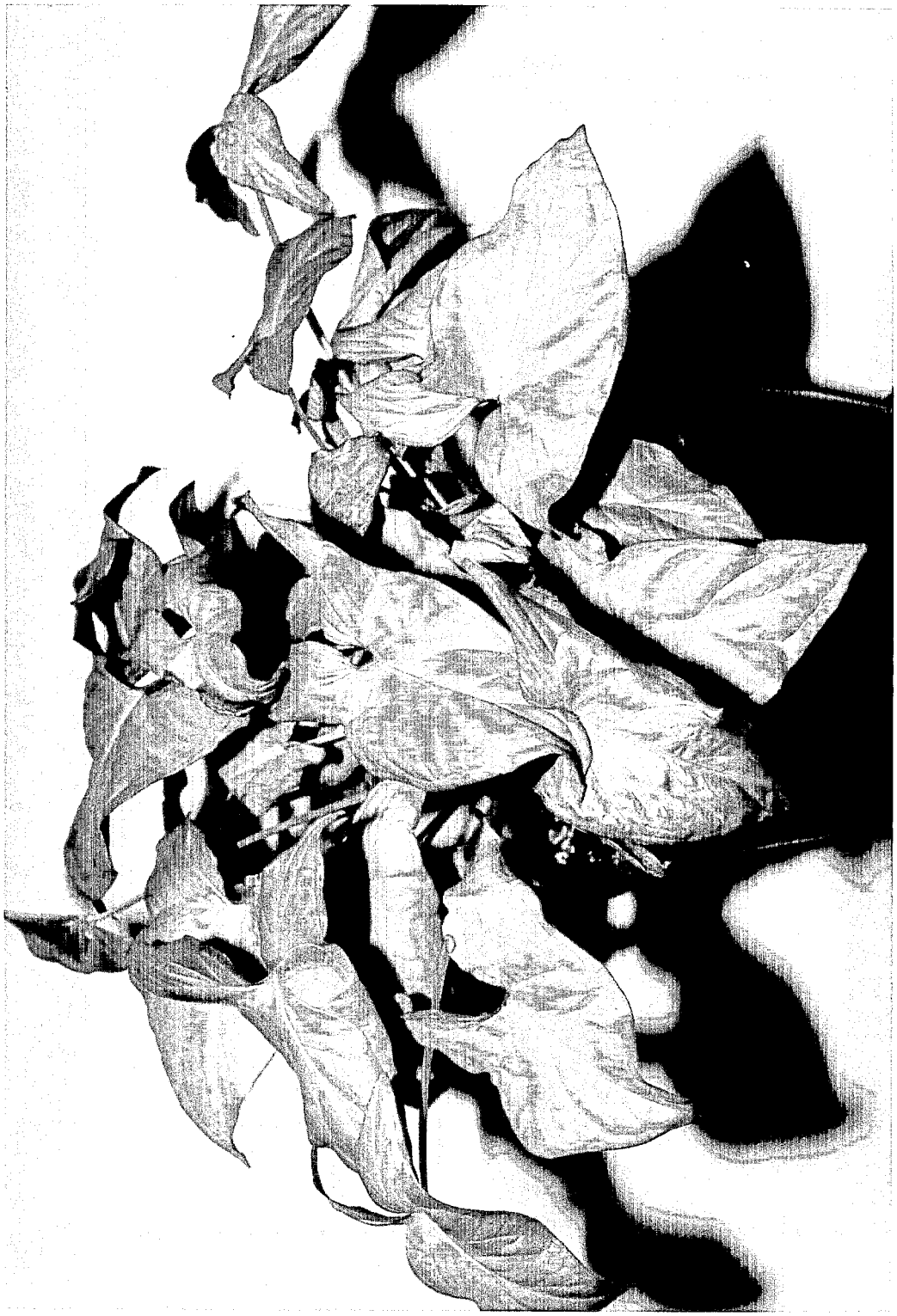

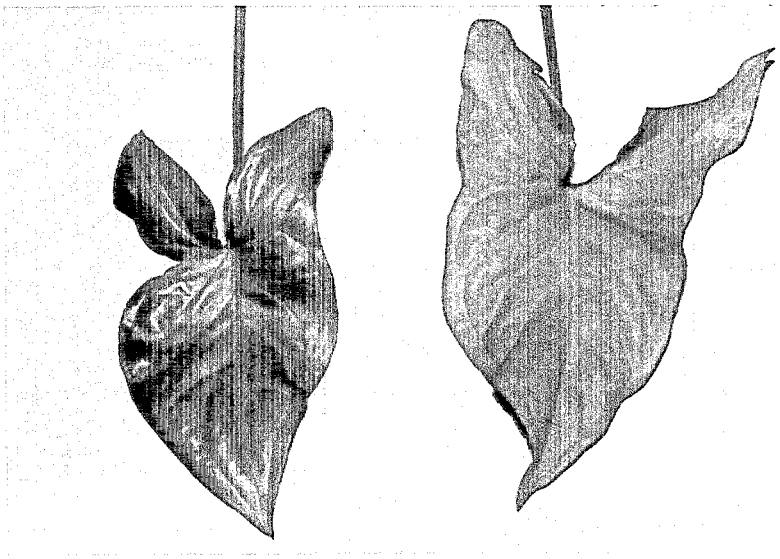

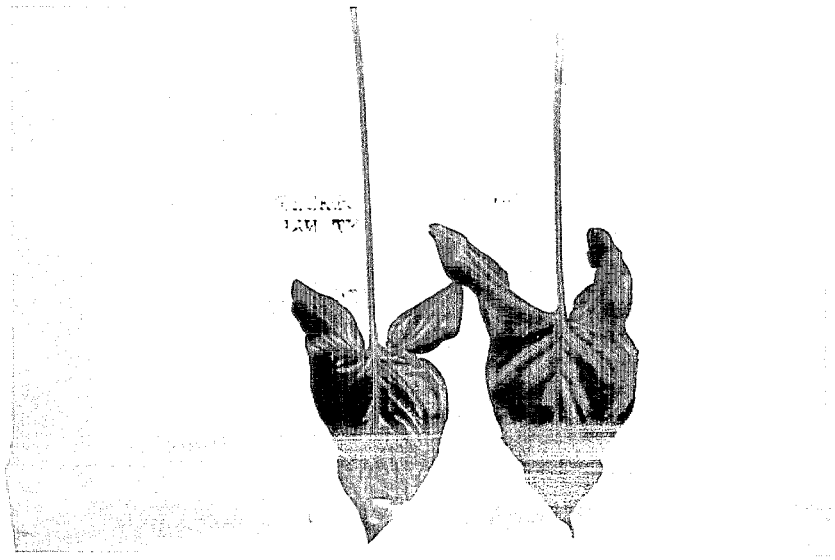

* * * * *